United States Patent

(12) United States Patent
Bahrami et al.

(10) Patent No.: US 8,298,774 B2
(45) Date of Patent: Oct. 30, 2012

(54) DIAGNOSIS OF SEPTIC COMPLICATIONS

(75) Inventors: Soheyl Bahrami, Götzendorf (AT);
Wolfgang Woloszczuk, Vienna (AT);
Gerhard Hawa, Vienna (AT)

(73) Assignee: Biomedica Medizinprodukte GmbH & Co KG, Vienna (AT)

( * ) Notice: Subject to any disclaimer, the term of this patent is extended or adjusted under 35 U.S.C. 154(b) by 350 days.

(21) Appl. No.: 12/530,732

(22) PCT Filed: Mar. 6, 2008

(86) PCT No.: PCT/AT2008/000082
§ 371 (c)(1),
(2), (4) Date: Mar. 15, 2010

(87) PCT Pub. No.: WO2008/109903
PCT Pub. Date: Sep. 18, 2008

(65) Prior Publication Data
US 2012/0094314 A1    Apr. 19, 2012

(30) Foreign Application Priority Data
Mar. 12, 2007 (AT) ................................. A 389/2007
Nov. 19, 2007 (EP) .................................... 07450202

(51) Int. Cl.
*G01N 33/53* (2006.01)
*G01N 33/542* (2006.01)
(52) U.S. Cl. .......................................... 435/7.1; 435/7.9
(58) Field of Classification Search .................. None
See application file for complete search history.

(56) References Cited

U.S. PATENT DOCUMENTS
2005/0148029 A1 *  7/2005  Buechler et al. ............... 435/7.1

FOREIGN PATENT DOCUMENTS
WO    WO 01/14885 A2    3/2001
WO    WO 2006/071583 A2    7/2006

OTHER PUBLICATIONS

Hama et al (Biochemical and Biophysical Research Communications vol. 198, No. 3, pp. 1177-1182, 1994).*
Bahrami, S., et al., "Plasma NT-proCNP Levels Differ in Multiply Traumatized Patients with or Without Septic Complications," Inflammation Research, vol. 56, Sup. No. 2, Mar. 2007, pp. S104 (XP008082913) Abstract.
International Preliminary Report on Patentability of PCT/AT2008/000082 dated Sep. 15, 2009.
International Search Report of PCT/AT2008/000082 dated Aug. 22, 2008.
Prickett TCR, et al., "C-Type Natriuretic Peptide (CNP) and Amino Terminal Pro C-type Natriuretic Peptide (NT-pro-CNP) in a sheep model of mild sepsis," Proceedings of the Scientific Meeting and 32rd Annual General Meeting of the ChristChurch Medical Research Society, pp. 1-6 (Apr. 24, 2002).

* cited by examiner

*Primary Examiner* — Albert Navarro
(74) *Attorney, Agent, or Firm* — Morgan, Lewis & Bockius LLP

(57) ABSTRACT

The invention describes a method for diagnosing of septic complications in polytraumatised human or animal patients, said patients being free of traumatic brain injury, by determining the level of the C-type natriuretic peptide (CNP), its precursors or fragments thereof, especially the precursor of the C-type natriuretic peptide (NT-proCNP), in this patient and diagnosing the patient a having septic complications or being at risk of developing septic complications, if the level of CNP, its precursors or fragments thereof, especially NT-proCNP, is increased compared to normal levels.

8 Claims, 4 Drawing Sheets

Figure 2B:
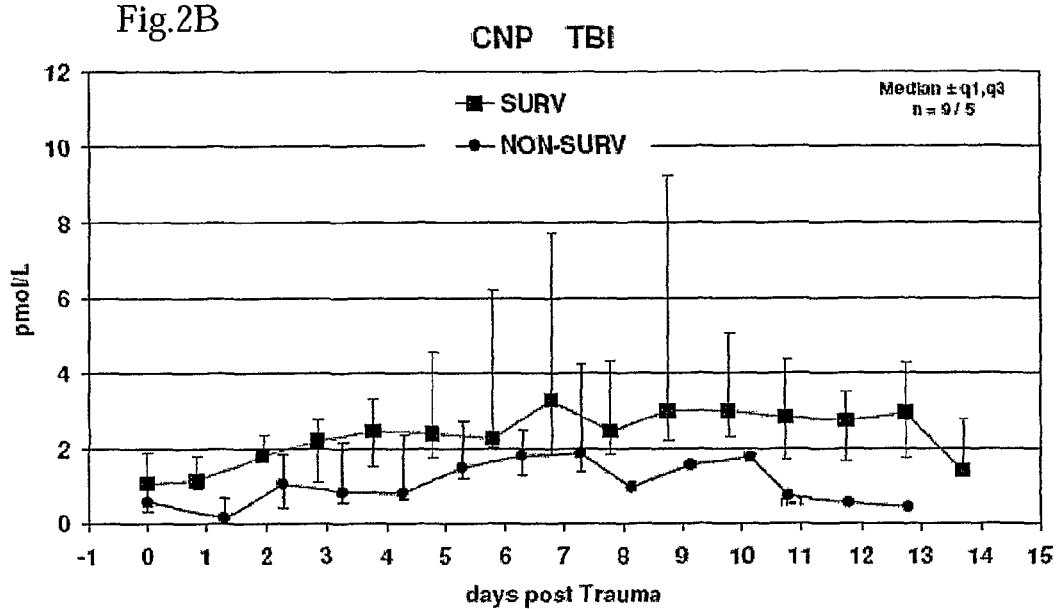

Fig.1A
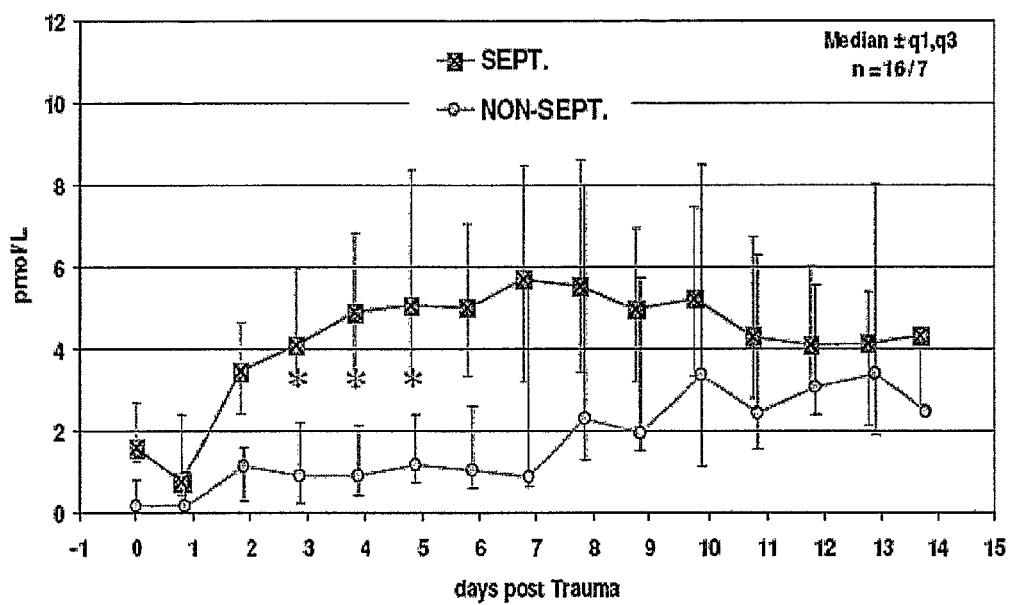
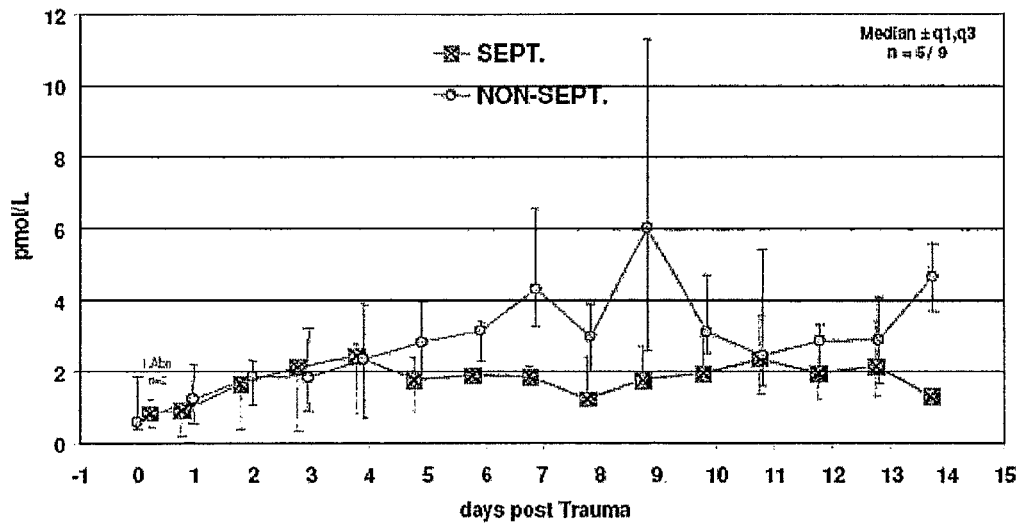
Fig.1B

Fig.1C
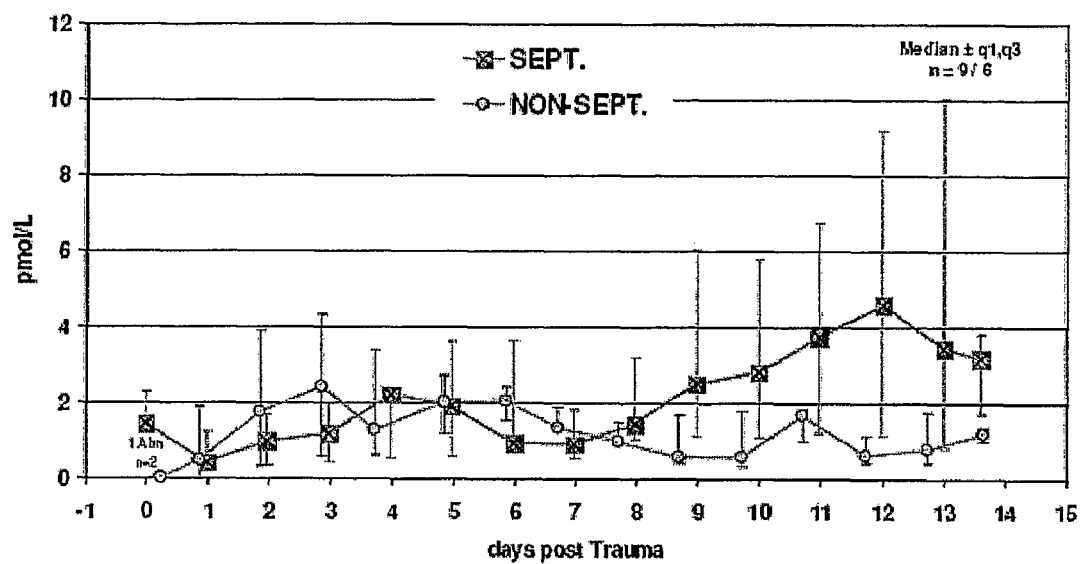
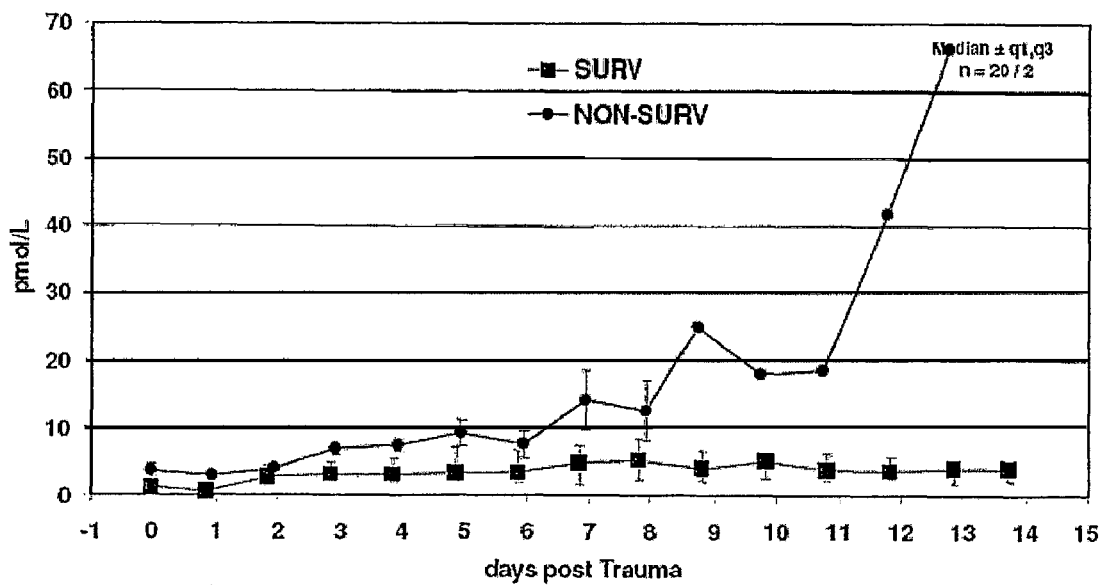
Fig.2A

SEQUENCE LISTING

<160> NUMBER OF SEQ ID NOS: 12

<210> SEQ ID NO 1
<211> LENGTH: 19
<212> TYPE: PRT
<213> ORGANISM: Homo sapiens

<400> SEQUENCE: 1

Lys Pro Gly Ala Pro Pro Lys Val Pro Arg Thr Pro Pro Ala Glu Glu
1               5                   10                  15

Leu Ala Glu

<210> SEQ ID NO 2
<211> LENGTH: 19
<212> TYPE: PRT
<213> ORGANISM: Rattus sp.

<400> SEQUENCE: 2

Lys Pro Gly Thr Pro Pro Lys Val Pro Arg Thr Pro Pro Gly Glu Glu
1               5                   10                  15

Leu Ala Glu

<210> SEQ ID NO 3
<211> LENGTH: 19
<212> TYPE: PRT
<213> ORGANISM: Bos sp.

<400> SEQUENCE: 3

Lys Pro Gly Ala Pro Pro Lys Val Pro Arg Thr Pro Ser Gly Glu Glu
1               5                   10                  15

Val Ala Glu

<210> SEQ ID NO 4
<211> LENGTH: 19
<212> TYPE: PRT
<213> ORGANISM: Ovis aries

<400> SEQUENCE: 4

Lys Pro Gly Ala Pro Pro Lys Val Pro Arg Thr Pro Pro Gly Glu Glu
1               5                   10                  15

Val Ala Glu

<210> SEQ ID NO 5
<211> LENGTH: 19
<212> TYPE: PRT
<213> ORGANISM: Mus sp.

<400> SEQUENCE: 5

Lys Pro Gly Thr Pro Pro Lys Val Pro Arg Thr Pro Pro Gly Glu Glu
1               5                   10                  15

Leu Ala Asp

<210> SEQ ID NO 6
<211> LENGTH: 19
<212> TYPE: PRT
<213> ORGANISM: Sus sp.

```
<400> SEQUENCE: 6

Lys Pro Gly Ala Pro Pro Lys Val Pro Arg Thr Pro Pro Gly Glu Glu
1               5                   10                  15

Val Ala Glu

<210> SEQ ID NO 7
<211> LENGTH: 21
<212> TYPE: PRT
<213> ORGANISM: Homo sapiens

<400> SEQUENCE: 7

Gly Asp Lys Ala Pro Gly Gly Gly Ala Asn Leu Lys Gly Asp Arg
1               5                   10                  15

Ser Arg Leu Leu Arg
            20

<210> SEQ ID NO 8
<211> LENGTH: 21
<212> TYPE: PRT
<213> ORGANISM: Rattus sp.

<400> SEQUENCE: 8

Gly Asp Lys Thr Pro Gly Gly Gly Ala Asn Leu Lys Gly Asp Arg
1               5                   10                  15

Ser Arg Leu Leu Arg
            20

<210> SEQ ID NO 9
<211> LENGTH: 21
<212> TYPE: PRT
<213> ORGANISM: Bos sp.

<400> SEQUENCE: 9

Gly Asp Lys Thr Pro Gly Gly Gly Ala Asn Leu Lys Asp Asp Arg
1               5                   10                  15

Ser Arg Leu Leu Arg
            20

<210> SEQ ID NO 10
<211> LENGTH: 21
<212> TYPE: PRT
<213> ORGANISM: Ovis aries

<400> SEQUENCE: 10

Gly Asp Lys Thr Pro Gly Gly Gly Ala Asn Leu Lys Asp Asp Arg
1               5                   10                  15

Ser Arg Leu Leu Arg
            20

<210> SEQ ID NO 11
<211> LENGTH: 21
<212> TYPE: PRT
<213> ORGANISM: Mus sp.

<400> SEQUENCE: 11

Gly Asp Lys Thr Pro Gly Ser Gly Ala Asn Leu Lys Gly Asp Arg
1               5                   10                  15

Ser Arg Leu Leu Arg
            20
```

-continued

```
<210> SEQ ID NO 12
<211> LENGTH: 21
<212> TYPE: PRT
<213> ORGANISM: Sus sp.

<400> SEQUENCE: 12

Gly Asp Lys Thr Pro Gly Gly Gly Gly Ala Asn Leu Lys Gly Asp Arg
1               5                   10                  15

Ser Arg Leu Leu Arg
            20
```

DIAGNOSIS OF SEPTIC COMPLICATIONS

This patent application claims the filing-date of the International PCT Application No. PCT/AT2008/000082, filed Mar. 6, 2008, which claims priority to Austrian Application No. A389/2007, filed Mar. 12, 2007, and European Patent Application No. EP07450202.2, filed Nov. 19, 2007. The disclosure of each of the above-identified applications is incorporated herein in its entirety.

The present invention relates to the diagnosis of septic complications.

The term "sepsis" has been used to describe a variety of clinical conditions related to systemic manifestations of inflammation accompanied by an infection. Because of clinical similarities to inflammatory responses secondary to non-infectious aetiologies, identifying sepsis has been a particularly challenging diagnostic problem. In this respect, definitions have been provided for "Systemic Inflammatory Response Syndrome" (or "SIRS"), which refers generally to a severe systemic response to an infectious or non-infectious insult, and for the related syndromes "sepsis," "severe sepsis," and "septic shock (Bone et al., Chest 101:1644-53, 1992). SIRS may be related to both infection and to numerous non-infective aetiologies, including trauma.

Despite the availability of antibiotics and supportive therapy, sepsis represents a significant cause of morbidity and mortality. Several laboratory tests have been investigated for use, in conjunction with a complete clinical examination of a subject, for the diagnosis/prognosis of sepsis (Giamarellos-Bourboulis et al., Intensive Care Med. 28: 1351-56, 2002).

Several molecular markers have been discussed to facilitate diagnosis and treatment monitoring of sepsis in humans and several animal species. The most widely used ones may be CRP (C-reactive protein) and PCT (procalcitonin). Also various interleukins have been discussed as potential biomarkers of sepsis. However they are of limited use at present because of a lack of specificity. For example, Carrigan et al. (Clinical Chemistry 50 (8) (2004) 1301-1314) reported the following sensitivities and specificities for these markers in humans:

These data show that even in humans, where septic disease patterns are extensively investigated, sensitivity and specificity of current markers can (even as mean values) come done to as low as 33% and 66% respectively, not to mention the in homogeneity of presently published data.

These data show that there is definitely a need for new diagnostic markers with improved clinical characteristics. Therefore, the diagnosis of sepsis, especially early diagnosis of sepsis, is still a great need in clinical medicine. An optimum diagnosis should reveal persons with a risk of developing sepsis or persons being at an early stage of sepsis. The use of CNP and NT-proCNP in animal sepsis models or as sepsis markers has been suggested or disclosed in WO 01/14885 A2, Hama et al. (BBRC 198 (3) (1994): 1177-1182), Prickett et al. (The New Zealand Medical Journal 115 (1157) (2002): page 6) or WO 2006/071583 A2.

However, diagnosis of sepsis turned out to be diverse and complicated in specific areas, especially in intensive care medicine. In these areas, sepsis markers described are often not reliable enough. Specifically in multiply traumatised patients such a diagnosis is often very difficult because of other pathological processes interfering with the "normal" physiological values and parameters measured in standard intensive care medicine.

Diagnosis of septic complications in polytraumatised patients is a very specific problem for which a high need exists in intensive care medicine.

It is therefore an object of the present invention to provide a suitable method for diagnosing sepsis in patients which are already in intensive care, specifically in polytraumatised patients.

Accordingly, the present invention provides a method for diagnosing of septic complications in polytraumatised human patients, said patients being free of traumatic brain injury, by determining the level of the human. C-type natriuretic peptide (CNP) or its precursors or fragments thereof, especially the N-terminal fragment of the precursor of the C-type natriuretic peptide (NT-proCNP) in this patient and diagnosing the patient having septic complications or being at risk of developing septic complications, if the level of NT-proCNP is increased compared to normal levels.

TABLE 1

ROC analysis results for various biomarker-based prediction of sepsis in adult and neonatal cases.[a]

| Marker | Age group | Cutoff range | ROC analysis Sensitivity, % | Specificity, % | Referenced studies |
|---|---|---|---|---|---|
| TNFα | Adults | 11.5 ng/L | 55 | 66 | (30) |
|  | Neonates | 12-20 ng/L | 67/79/88 | 43/71/86 | (29, 61 63) |
| IL-G | Adults | 50-200 ng/L | 51/67/86 | 53/65/79 | (30, 35, 36, 66) |
|  | Neonates | 10-100 ng/L | 71/84/100 | 43/71/96 | (28, 29, 61, 63, 70-72) |
| IL-1ra | Children | NA[b] | 33 | 89 | (85) |
|  | Neonates | 10.9 μg/L | 93 | 92 | (70) |
| IL-8 | Adults | 20-340 ng/L | 57/63/68 | 57/76/93 | (30, 35, 85) |
|  | Neonates | 50 ng/L | 92 | 70 | (61) |
| CRP | Adults | 4-150 mg/L | 35/69/89 | 18/61/81 | (30, 35, 36, 38, 46, 66, 88, 89) |
|  | Neonates | 1-23 mg/L | 43/65/96 | 80/90/100 | (22, 26, 63, 70, 89, 90) |
| PCT | Adults | 0.4-8.1 μg/L | 65/81/97 | 48/73/94 | (30, 35-38, 43, 46, 66, 88, 89, 122, 123) |
|  | Neonates | 1.0-6.1 μg/L | 77/85/99 | 62/83/91 | (22, 72, 88, 90) |

[a]Values listed are for differentiating infected individuals from uninfected controls rather than from healthy individuals. Sensitivities and specificities listed are minimum, mean (in bold), and maximum percentages.
[b]NA, not available.

Specifically in intensive care medicine of human patients, CNP turned out to be an excellent diagnostic tool for diagnosing of septic complications in polytraumatised patients, however, surprisingly the present diagnosis has a high reliability and excellent robustness only for those patients which are free of traumatic brain injury.

Within the course of the present invention, clinical data were collected which show that the use of human CNP, its precursors or fragments of these precursors is beneficial for identifying patients with sepsis in a specific group of patients, especially early stage sepsis or even persons with a risk of developing sepsis. Specifically NT-proCNP, the N-terminal fragment of the C-type natriuretic peptide (CNP) precursor has proven to be a suitable diagnostic/prognostic marker related to sepsis in the stratification of risk of sepsis in multiply traumatised patients. This molecule is specifically suitable due to its stability, abundance and easiness for becoming detected.

Natriuretic peptides play an important role in sodium regulation and blood pressure control. CNP is a member of the natriuretic peptide family which is produced in vascular endothelial cells and may play an important paracrine role in the vasculature. The atrial natriuretic peptide (ANP) and brain natriuretic peptide (BNP) strongly stimulate the secretion of CNP. BNP causes much greater stimulatory effect than the ANP, and ANP also significantly enhanced the production of new CNP protein (translation) and mRNA expressed in the bovine arterial endothelial cells.

Plasma natriuretic peptide levels are influenced by a number of factors including age and gender. In a healthy population, plasma levels of N-terminal ANP (NT-ANP), BNP and NT-BNP were variably influenced by clinical covariates. While all three peptides were higher in women, only NT-ANP and NT-BNP were influenced by age. Levels of all peptides were inversely correlated with heart rate. In contrast to NT-ANP and NT-BNP, plasma BNP was not influenced by age. Plasma natriuretic peptide levels have been considered for the diagnosis of heart failure. BNP and NT-ANP were noted being markedly elevated in the majority of patients with pacemakers. Plasma N-terminal proBNP concentrations have been reported to increase as a result of impaired systolic function, age, impaired renal function, cardiac ischemia and enlargement, and certain medications. An increase in plasma N-terminal proBNP has been considered as an earlier sign of abnormal cardiac function than abnormalities identified by echocardiographic measurements. In this respect, it has been suggested that consideration of both NT-ANP and NT-BNP identifies a greater number of patients at risk of death or heart failure than either peptide alone (Squire I B et al. (Clin Sci (Lond). 2004 September; 107(3):309-16)).

CNP has been shown to be produced by the heart in patients with chronic heart failure but to a much lesser extent than ANP or BNP. Furthermore it expressed in high amounts in the brain and the Endothelium. The potential of plasma amino-terminal C-type natriuretic peptide (NT-CNP) as a marker of cardiac function was investigated in symptomatic patients. These findings suggest a possible compensatory response from the peripheral vasculature to heart failure by the endothelium-based vasodilator peptide CNP.

Whereas CNP can be applied on a broad basis in humans and animals as a marker for sepsis, it should be kept in mind that presence of specific indications have always to be considered where a single marker is not necessarily sufficient due to specific circumstances which could hide or counter-act a marker function of a given marker.

It was, however, surprising that this CNP, its precursors and fragments thereof, especially NT-proCNP, are suitable markers for sepsis in polytraumatised human patients. Remarkably, the relevance of sepsis diagnosis according to the present invention in polytraumatised human patients is significantly pronounced in a specific group of patients: polytraumatised (i.e. multiply traumatised) patients (i.e. patients with more than one trauma), except patients with traumatic brain injury. In a study performed in the course of the present invention, the long term profiles of NT-proCNP, the N-terminal fragment of the CNP precursor, in multiply traumatised patients with and without traumatic brain injury (TBI) was examined with relationship to septic complications and outcome (NT-proCNP was chosen because it circulates in higher amounts and is more stable than the active hormone CNP, nevertheless all CNP precursors and fragments thereof (if detectable in principle in a patient) can be used in principle for the assessment according to the present invention, yet the use of stable and easy-to-detect forms is of course preferred for the use in clinical practice). Multiply traumatised patients (MTP) with or without TBI verified by computer tomography were assessed with respect to their NT-proCNP-profiles. Distinct NT-proCNP profiles in patients with or without TBI were surprisingly found. While NT-proCNP levels were significantly higher in MTP developing septic complication without TBI, NT-proCNP levels were lower in MTP with TBI developing septic complications. In non-survivors NT-proCNP levels increased dramatically before death. Remarkably, NT-proCNP plasma profiles differ distinctly between MTP with and without TBI, developing septic complications.

The terms "sepsis" or "septic complications" are used synonymously in the present application and are understood to encompass "sepsis", "septic complications", "severe sepsis", "septic shock", "Systemic Inflammatory Response Syndrome" (or "SIRS") and even earlier stages thereof, all symptoms being related to systemic manifestations of inflammation accompanied by an infection.

Of course, the present diagnosis is applied on polytraumatised patients who are suspected to have septic complications and/or patients who are at risk of developing septic complications. Diagnosis according to the present invention is always made with a view to the septic complications. This is self-understanding in view of the diagnostic history of CNP being known as a marker for chronic heart failure. Also in that connection, CNP levels have been analysed with a view to cardiac function to correlate this CNP marker with other diagnosis markers. Therefore, the present sepsis diagnosis using CNP as a marker is not necessarily suitable as an "absolute" marker, but is useful for serving in the diagnosis whether sepsis is present or to be expected in a patient or not. This diagnosis question is, however, only asked, if septic complications are suspected or there is a risk of sepsis in a given patient.

Preferably, the level of CNP, its precursors or fragments thereof, especially NT-proCNP, in a patient is determined by determining the amount of CNP, its precursors or fragments thereof, especially NT-proCNP, in a blood, serum or plasma sample of the patient. Although determination of this level according to the present invention is also possible in other tissue or body fluids of the patients (e.g. in liquor, lymph fluid, urine, etc.), samples derived from the blood of the patients are preferred, because such samples are present anyway and levels of the marker according to the present invention are easily detectable. Tissue samples are usually not practical in view of the intensive care patients' general state.

In the method according to the present invention the determined level of CNP, its precursors or fragments thereof, especially NT-proCNP, is usually compared to "normal" levels by routine methods (e.g. by knowledge of the normal levels or by directly comparing the determined level to levels measured in patients without sepsis or without risk of developing sepsis). This comparison can also be made to comparing previous determinations of the same, patient showing "normal" levels. On the other hand, the diagnosis may also be based on the knowledge or parallel determinations of "sepsis" levels of CNP, its precursors or fragments thereof, especially NT-proCNP (e.g. of patients having already developed sepsis). Therefore, a preferred method according to the present invention is characterised in that the normal level is the level of a polytraumatised patient without having septic complications or without being at risk of developing septic complications.

It is also possible to compare the result of the CNP determination to absolute values, if the method for determination is suitable to provide such absolute values. Also here, the use of NT-proCNP is preferred, because such absolute values (or: critical values above which indication of sepsis is likely) can easily be provided for this fragment of pre-proCNP (the precursor of CNP and NT-proCNP). For example for Eurasians "normal" lengths of NT-proCNP are within 2-2.5 pico-mol/l. Increased levels (e.g. preferably at least 50% above the normal level, more preferred at least 70% above the normal level, especially at least 100% above the normal level (normal level of a given set of people normally used in medical diagnostics (e.g. race, risk-factors (nutritional behaviour, etc.)) are indicative for the method of the present invention for diagnosing septic complications. Accordingly, it is preferred that the patient is diagnosed to have septic complications or is at risk of developing septic complications, if the level of NT-proCNP is higher than 4 pM (pico-mol/l).

Preferably, NT-proCNP is determined by using anti-NT-proCNP antibodies. Of course, any other of CNP, its precursors or fragments thereof is also preferably determined using specific anti-bodies thereto.

Sepsis is also a problem in veterinary medicine, i.e. for non-human animals as patients ("animal-patients"). In veterinary medicine there is research on basically the same parameters as used in human medicine. For example, in the study of Pusterla et al. (Am. J. Vet. Res. 67(6) (2006), 1045-1049), TNF-alpha, interleukin (IL)-1beta, IL-6, IL-8, IL-10, procalcitonin (PCT), and transforming growth factor (TGF)-beta have been investigated by PCR methods. However, well established immunoassays with sufficient cross reactivity or specific for the analogues molecule circulating in various animal species are still missing yet. This lack of suitable assays is very surprising, because there is an urgent need larger market for such tests, especially for companion animals like dogs, cats and horses. People are willing to spend high amounts on animal care because of emotional relationship to the pets or because of the value of the animals (racing sports, valuable breed animals; for example, in 2006, US citizens spent 38.5 billion US for their pets. About a quarter of that sum was used for veterinary services. It follows that also in the veterinary field, suitable diagnosis of sepsis is highly needed.

Accordingly, the present invention provides a method for diagnosing of septic complications in polytraumatised animal patients, said patients being free of traumatic brain injury, by determining the level of the C-type natriuretic peptide (CNP) or its precursors or fragments thereof, especially the N-terminal fragment of the precursor of the C-type natriuretic peptide (NT-proCNP) in this patient and diagnosing the patient having septic complications or being at risk of developing septic complications, if the level of NT-proCNP is increased compared to normal levels.

Preferred animal patients to be diagnosed according to the present invention are mammals of high scientific or individual value, especially cattle, deer, zoo animals, pets, laboratory animals or working animals. Of course, the invention is restricted to animals having CNP, especially in a comparable function to humans. Animal patients which are specifically preferred in the present invention are bovine, sheep, goat, horse, donkey, yak, pig, rat, mouse, cat, dog, hamster, fish, frogs, reptiles, guinea pig, elephant, bear or monkey patients. In fact, the surprisingly good reactivity of the human antibodies despite the sequence discrepancies with the canine/feline NT-proCNP or with other animal NT-proCNP (and vice versa) shows that the assay according to the present invention may work on all animals where CNP is known to be present (even with cross reacting antibodies from differing species).

In clinical practice, especially in intensive care medicine, NT-proCNP is preferably determined by using an immunoassay kit for human or animal NT-proCNP. For this purpose, an immunoassay for human or animal NT-proCNP or an antigenic fragment thereof or even a polypeptide extension thereof lacking CNP activity wherein the primary binding partner therefore is a monoclonal or polyclonal antibody to these molecules may be used according to the present invention. Methods of immunoassay are of course well known in the art eg. RIA, ELISA, fluorescence immunoassay (FIA) or dry chemistry test strip immunoassays. Such an immunoassay will, in general, use a monoclonal or polyclonal antibody against CNP, its precursors or fragments thereof, especially NT-proCNP, in a method according to the present invention in immobilised form, e.g. on microtiter plates, membranes or beads, to isolate e.g. the target NT-proCNP compound. In a sandwich assay, the bound antigen may be labelled using additional soluble anti-body according to the invention, which may be monoclonal or polyclonal and which may either carry a label or, more conveniently, may itself be labelled subsequently by reaction with a secondary antibody carrying a label.

A specifically preferred immunoassay is the NT-proCNP assay developed by Biomedica Gruppe (AT) based on polyclonal anti-NT-proCNP antibody-precoated microtiter devices.

Thus, if the primary antibody according to the invention is raised in mice or rabbits, the labelled secondary antibody may be an anti-mouse or anti-rabbit antibody.

Suitable labels include radionuclides, fluorescent substances eg. Europium based fluorogens, enzymes, for example as used in ELISA systems employing automated hybrid methods or dyes or coloured particles such as colloidal gold.

Alternatively, a competitive binding assay may be used, wherein a known quantity of e.g. labelled human NT-proCNP or antigenic fragment or inactive extension thereof, is added to the analyte solution and contacted with a limited quantity of the immobilised monoclonal or polyclonal antibody, whereby the amount of labelled antigen which is immobilised is inversely proportional to the amount of target antigen present in the analyte.

The invention also comprises the use of a kit for immunoassay of human or animal CNP, its precursors or fragments thereof, especially NT-proCNP, for the diagnosing method according to the present invention, the kit comprising:

(a) a monoclonal or polyclonal antibody to CNP, its precursors or fragments thereof, especially NT-proCNP, in immobilised form and, at least one further component selected from;

(b) a labelled sample of CNP, its precursors or fragments thereof, especially NT-proCNP;

(c) said monoclonal or polyclonal antibody in non-immobilised form;

(d) a labelled secondary antibody specific to said antibody (c).

The present invention therefore has significant use especially in the in hospital intensive care setting where monitoring of this parameter is advantageous.

As stated above, the body fluid on which the immunoassay is performed may be any body fluid in which the human or animal NT-proCNP is located, but conveniently will be plasma or serum. In some cases it may be convenient to extract the peptide, or otherwise treat the sample prior to assay.

The CNP, its precursors or fragments thereof, especially NT-proCNP, and antibodies thereto in the kits for diagnosing animal patients according to the present invention have to be provided either with the homologous protein(s) (including the precursors or fragments) and antibodies thereto or with heterologous proteins (i.e. CNP, its precursors or fragments from another species) which enable cross-reactive antibodies. Accordingly, the kit according to the present invention can, especially for animal patients, contain the homologous CNP, its precursors or fragments thereof, especially NT-proCNP, and monoclonal and/or polyclonal antibodies to such homologous CNP, its precursors or fragments thereof, or contain heterologous CNP standards and cross-reactive antibodies. It was specifically surprising that e.g. a dog or cat CNP protein or peptide can be recognized by an e.g. human antibody against CNP, because—despite relatively high homologies between CNP from various animals and human—for e.g. proANP 1 or 2 amino acid exchanges have shown to be sufficient for completely eliminating immune reactivity.

The invention is further described by the following examples and the drawing figures, yet without being restricted thereto.

Figure 2C:
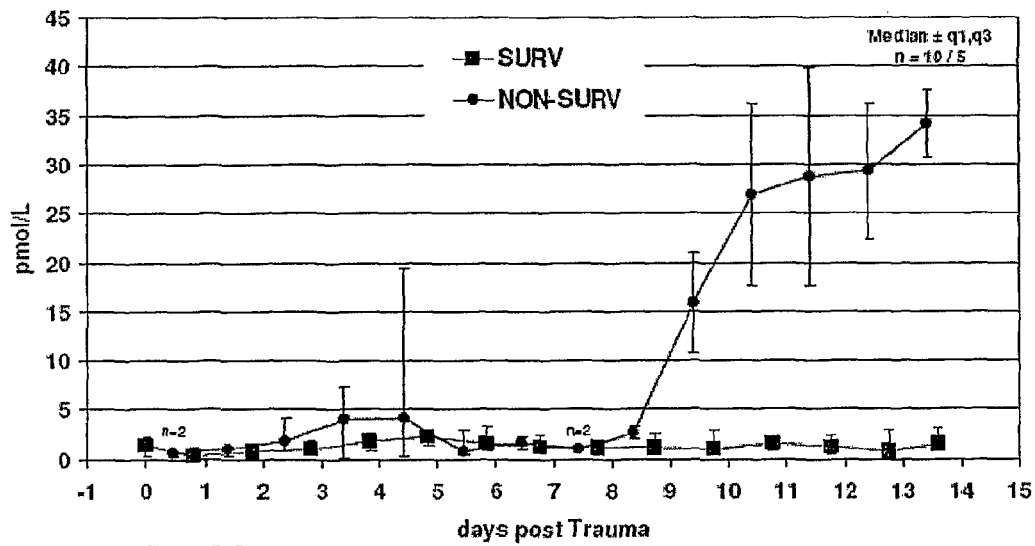
Figure 3A:
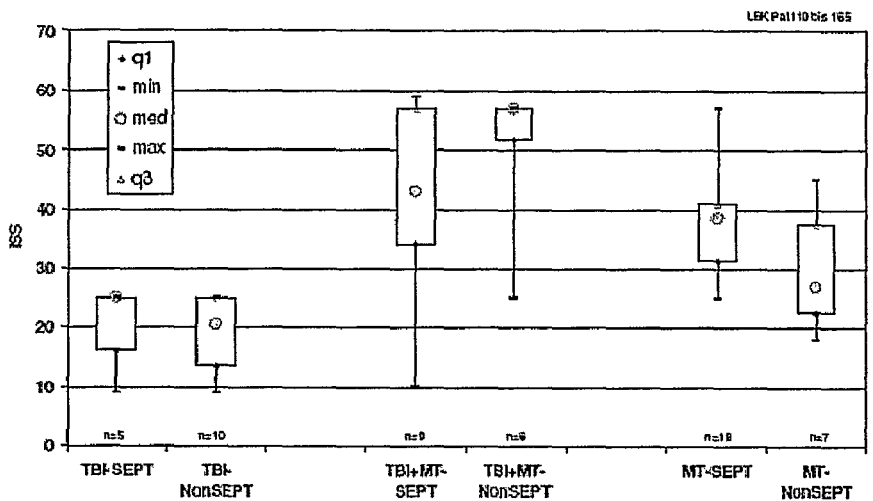
Figure 3B:
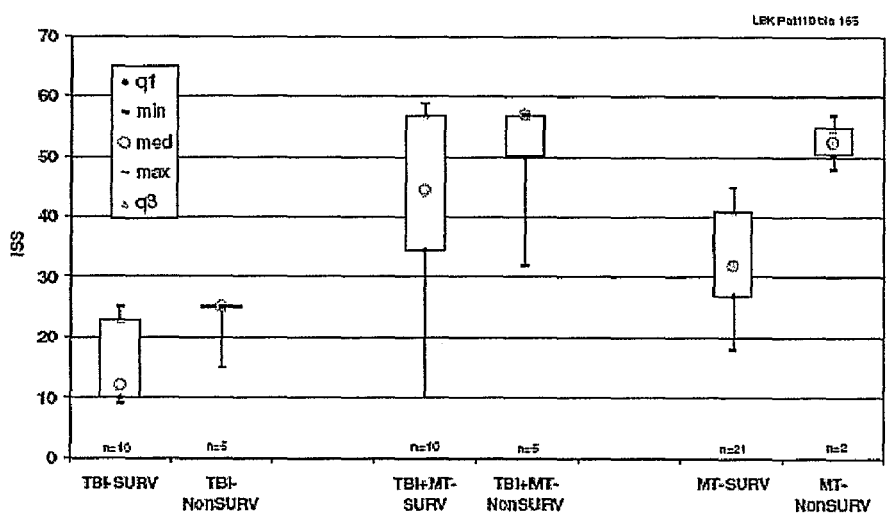
Figure 3C:
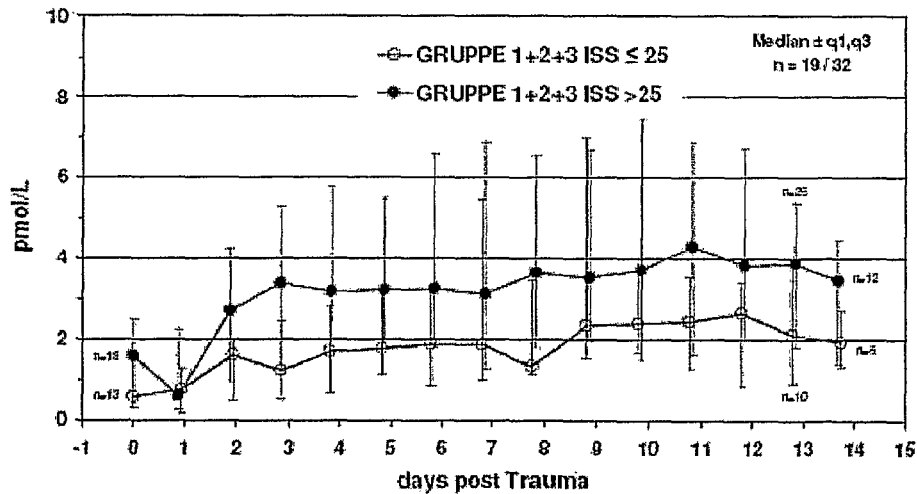

FIG. 1 shows the CNP profile in MT patients without TBI with/without septic complications (FIG. 1A), the CNP profile in MT patients with isolated TBI with/without septic complications (FIG. 1B) and the CNP profile in MT patients with TBI with/without septic complications (FIG. 1C);

FIG. 2 shows the CNP profile in MT patients without TBI (survivors/non-survivors; FIG. 2A), the CNP profile in TBI patients (survivors/non-survivors; FIG. 2B) and the CNP profile in TBI plus MT patients (survivors/non-survivors; FIG. 2C);

FIG. 3 shows the ISS≦25 versus ISS≧25 (sepsis/non-sepsis; FIG. 3A), ISS≦25 versus ISS≦25 (survival/non-survival; FIG. 3B) and, the related CNP profile by ISS≦25 versus ISS≦25 (FIG. 3C).

EXAMPLES

Example 1

Clinical Study in Polytraumatised Patients

A clinical study was performed by using the method according to the present invention. In the present study the long term profiles of NT-proCNP, the N-terminal fragment of the CNP precursor, in multiply traumatised patients with and without traumatic brain injury (TBI) with relationship to septic complications and outcome were determined (as stated above, NT-proCNP was chosen because it circulates in higher amounts and is more stable than CNP).

Patients and Methods

The study protocol is in accordance with the standards of the Declaration of Helsinki. Following approval by the Ethics Committee of the Allgemeine Unfallversicherungsanstalt this retrospective study was carried out in all patients admitted to either of the two participating level 2 trauma centers from February 2002 to September 2003. The following criteria were required for inclusion: isolated TBI, multiple trauma without (MT) or with TBI (TBI+MT), admission to the trauma center within 8 hours after trauma, first blood sample drawn within 12 hours after trauma, Patient age >17 years, Injury Severity Score (ISS)>16, treatment in the intensive care unit required. TBI was defined as trauma to the brain with an Abbreviated Injury Score (AIS)≧verified by computer-assisted tomography at admission. Sepsis was defined as the combination of at least 2 of the 4 criteria of systemic inflammatory response syndrome (SIRS) in combination with a septic focus or a positive blood culture for ±3 days. All retrospective NT-proCNP measurements were performed from blood sampled for routine evaluation.

Serum NT-proCNP was measured at admission and daily thereafter during the following time intervals: <12 hours, 12-24 hours, and days 2 to 16 after trauma. All measurements were based on the actual sample size at each time interval, since all patients did not survive until day 16 after trauma. Whole blood was sampled into sterile test tubes (Vacuette, Greiner Company, Vienna, Austria). Samples were centrifuged at 1500×g for 20 minutes and serum was stored at −70° C. NT-proCNP was measured (by NT-proCNP enzyme immunoassay of Biomedica (Austria). The lower detection threshold of the assay is 0.55 pico-mol/l and the normal range is 0 to 40 pico-mol/l.

Trauma management was carried out according to the Advanced Trauma Life Support guidelines and the trauma management protocol. Analgosedation with sufentanil (Janssen & Cilag Pharma, Vienna, Austria) and propofol (AstraZeneca, Vienna, Austria) was administered during ventilatory support and all patients received combined parenteral and enteral nutritional support. A Swan Gantz catheter (Arrow thermodilution catheter AH-05050®, Novomed Co, Vienna, Austria) was inserted when necessary to manage hemodynamically highly unstable patients. Ventricular and/or parenchymal catheters (Spiegelberg catheter 3PS®, Schwandtner Co., Linz, Austria) were used to measure intracranial pressure in patients with TBI. Laboratory checks as well as neurological follow-ups were carried out daily by the same neurologist and all patients were under clinical observation around the clock by the attending anaesthesiologists and nursing team.
Statistics:

Serum NT-proCNP levels were compared during the respective time intervals and statistically evaluated by Mann-Whitney U test regarding the occurrence of sepsis versus non-sepsis and mortality (non-survival versus survival) with isolated TBI, MT with or without TBI. Significance was corrected for multiple use according to Hochberg & Benjamini (Stat Med. 1990 9:(7):811-8). P<0.05 was considered statistically significant.

Cut-off NT-proCNP serum levels for sepsis prediction were determined separately for isolated TBI and for TBI with multiple trauma during different time intervals after trauma (<12 hours, 24 hours, and days 2 to 16 by receiver operating characteristic (ROC) curve analysis (Metz, Sem. Nucl. Med. 1978 8 (4): 283-298) of the maximum serum level during these time intervals after trauma. The ROC curve plots sensitivity against 100 minus specificity, using a range of "cut-off" values for a positive prediction. The area under the curve (AUC) is a measure of the accuracy of prediction with ≦0.5 by chance alone and increasing to 1 as the accuracy increases to 100% sensitivity and specificity. Since positive and negative predictive values vary with mortality, sensitivity and specificity were added to have a disease-prevalence independent parameter. Calculations were performed using Medcalc statistical software (Medcalc Software, Mariakerke, Belgium).

Results

The study included 53 patients whose demographic data are presented in Table 2.

TABLE 2

| Demographic data. | | | |
|---|---|---|---|
| | All Patients | Sepsis | Non-sepsis |
| Total (n) | 53 | 30 | 23 |
| Male (n) | 47 | 27 | 20 |
| Female (n) | 6 | 3 | 3 |
| Age (Median) | 36 | 36 | 38 |
| (q1, q3) | (32, 48) | (33, 44) | (25, 58) |
| TBI (n) | 15 | 5 | 10 |
| MT (n) | 23 | 16 | 7 |
| TBI + MT (n) | 15 | 9 | 6 |
| Cause of death TBI (n) | 7 | 1 | 6 |
| Cause of death MOF (n) | 5 | 4 | 1 |
| Survivors (n) | 41 | 25 | 16 |
| Non-Survivors (n) | 12 | 5 | 7 |
| ISS ≦ 25 (n) | 21 | 7 | 14 |
| ISS ≦ 25 (Median) | 20 | 25 | 19 |
| (q1, q3) | (15, 25) | (13, 25) | (15, 25) |
| ISS > 25 (n) | 32 | 23 | 9 |
| ISS > 25 (Median) | 41 | 41 | 50 |
| (q1, q3) | (34, 57) | (32, 46) | (41, 57) |
| SIRS | 39 | 30 | 9 |

NT-proCNP levels were significantly higher in MT patients without TBI developing septic complications than non-septic patients. NT-proCNP levels were even lower in MT patients with TBI developing septic complications than non-septic patients (FIGS. 1A,B). ROC curve analysis and calculation of the AUC of NT-proCNP for the prediction of sepsis in MT patients without TBI are presented in table 3. The AUC values were found between 0.653 to 0.875 on days two to eight after trauma (with a maximum achievable value of 1).

TABLE 3

Calculations according to receiver operating characteristic (ROC) curves

| Days after trauma | Disease prevalence | AUC ± SE | Confidence interval | Cut off value (pmol/L) | Sensitivity | Specifity |
|---|---|---|---|---|---|---|
| 0 | 71.4 | 0.762 | 0.468-0.940 | 0.23 | 90.0 | 75.0 |
| 1 | 72.7 | 0.755 ± 0.108 | 0.527-0.910 | 0.21 | 93.8 | 66.7 |
| 2 | 72.2 | 0.780 ± 0.101 | 0.556-0.926 | 1.60 | 87.5 | 83.3 |
| 3 | 69.6 | 0.857 ± 0.079 | 0.649-0.965 | 2.24 | 93.8 | 85.7 |
| 4 | 69.6 | 0.866 ± 0.076 | 0.660-0.969 | 2.20 | 87.5 | 85.7 |
| 5 | 69.6 | 0.875 ± 0.073 | 0.671-0.973 | 2.63 | 93.8 | 85.7 |
| 6 | 71.4 | 0.811 ± 0.096 | 0.583-0.945 | 1.04 | 100 | 66.7 |
| 7 | 71.4 | 0.711 ± 0.119 | 0.475-0.884 | 1.06 | 93.3 | 66.7 |
| 1 to 8 | 71.4 | 0.774 ± 0.036 | 0.705-0.834 | 2.31 | 81.6 | 76.0 |
| 2 to 8 | 71.2 | 0.797 ± 0.036 | 0.725-0.858 | 2.31 | 89.0 | 75.0 |

NT-proCNP levels were higher in non-survivors than survivors when multiple organ failure was the cause of death, but not when was TBI (FIGS. 2A, B). Plasma NT-proCNP levels in non-survivors with TBI+MT did not significantly differ compared to the survivors during all time intervals after trauma (FIG. 2C).

Comparing patients with or without septic complications, the ISS did not differ between groups with isolated TBI, TBI+MT, or MT without TBI (FIG. 3A). ISS was markedly higher in non-survivors versus survivors only in MT patients without TBI (FIG. 3B). NT-proCNP levels did not differ between patients with ISS below or above 16 (FIG. 3C).

Discussion

Few studies have compared the relative prognostic value of different natriuretic peptides in polytraumatised patients. The study according to the present invention relates to the identification and use of CNP, its precursors or fragments thereof, especially NT-proCNP, as diagnostic/prognostic marker related to sepsis in the stratification of risk of sepsis in multiply traumatised patients. According to the present invention CNP, its precursors or fragments thereof, especially NT-proCNP, has been investigated in multiply traumatised patients with and without traumatic brain injury (TBI) with relationship to septic complications and outcome. NT-proCNP was chosen because it circulates in higher amounts and is more stable than the active hormone CNP. In the present study it was shown that NT-proCNP plasma profiles differ distinctly between MT patients with and without TBI, developing septic complications. Starting on day two after trauma, plasma NT-proCNP levels were significantly higher in multiply traumatised patients without TBI, developing septic complications compared to non-septic patients. In patients with isolated TBI, developing sepsis the plasma NT-proCNP levels were even lower than in non-septic patients at all time points after trauma, indicating different underlying regulatory mechanisms in patients with or without TBI.

Comparing N-terminal ANP, BNP and CNP prohormones as early congestive heart failure indicators, the ProANPs 31-67 was found as the most sensitive marker in discriminating CHF subjects from healthy individuals. In congestive heart failure patients plasma CNP elevation has been related to clinical and functional disease severity. In patients with various cardiovascular disorders, the plasma level of CNP was found markedly increased in patients with septic shock, while there was no alteration in patients with congestive heart failure or hypertension but there was two-fold increase of the plasma CNP level in patients with chronic renal failure. In the study according to the present invention, ROC curve analysis and calculation of the AUC of NT-proCNP for the prediction of sepsis in MT patients without TBI revealed plasma NT-proCNP levels as a sensitive marker in discriminating patients with/without septic complications.

In the present study (in the meantime also published in Bahrami et al., Inflamm. Res. 56 (Suppl2) (2007): S104 (A81)), the post-traumatic septic complications in each group (TBI, MT, TBI+MT) were not related to the ISS. Similarly, plasma NT-proCNP levels were not associated with the ISS and did not differ between patients with ISS below or above 25.

In multiply traumatised non-survivors (n=2) without TBI, plasma NT-proCNP levels were dramatically increased before death. In contrast, in patients with isolated TBI plasma NT-proCNP levels were lower in non-survivors than survivors at all time points. However the differences did not reach significant levels, most likely because of limited number of patients in each group.

CNP, but not ANP or BNP, has been recognized to relax human resistance arteries by activating cyclic GMP-dependent kinase and BKCa2+ channels. In addition, CNP has been reported to increase myocardial contractile force with an increase in sinus rate mediated by guanylyl cyclase-linked natriuretic peptide receptors, probably type B receptors in the dog heart, and suggesting that the positive inotropic response to CNP is influenced by the cyclic adenosine 3',5'-monophosphate(cAMP)-dependent signal transduction. Since CNP is widely present in endothelium it may play a role in the regulation of peripheral resistance in man in physiological and pathological circumstances. The pathophysiologic relevance of CNP in septic setting is not clearly understood yet.

In summary, it could be shown with the present study that NT-proCNP plasma profiles differ distinctly between MTP with and without TBI, developing septic complications. According to the ROC curve analysis and calculation of the AUC for the prediction of sepsis in multiply traumatised patients without TBI plasma levels of CNP, its precursors or fragments thereof, especially NT-proCNP, are sensitive markers in discriminating patients with/without septic complications.

Example 2

Sepsis Diagnosis in Human and Animal Patients

From the results obtained from human serum/plasma samples, wherein the marker function of NT-proCNP for the diagnosis and treatment monitoring of sepsis was shown (see also: Example 1 above), the marker function of CNP for sepsis in animals was investigated.

The antibodies used for collecting those data are directed against amino acids 1-19 and 30-50 of human NT-proCNP.

The amino acid sequences of some species are available in the literature for which homology data have already been acquired. The following table summarises some of those data for the epitopes used in this investigation:

TABLE 4 amino acids 1-19 (A) and 30-50 (B) of human NT-proCNP and various animal species (A)

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| human propCNP | K | P | G | A | P | P | K | V | P | R | T | P | P | A | E | E | L | A | E |
| rat proCNP | K | P | G | | P | P | K | V | P | R | T | P | P | G | E | E | L | A | E |
| bovine proCNP | K | P | G | A | P | P | K | V | P | R | T | P | S | G | E | E | V | A | E |
| sheep proCNP | K | P | G | A | P | P | K | V | P | R | T | P | P | G | E | E | V | A | E |
| mouse proCNP | K | P | G | | P | P | K | V | P | R | T | P | P | G | E | E | L | A | D |
| pig proCNP | K | P | G | | P | P | K | V | P | R | T | P | P | G | E | E | V | A | E |

(B)

| | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|
| human propCNP | G | D | K | A | P | G | G | G | G | A | N | L | K | G | D | R | S | R | L | L | R |
| rat proCNP | G | D | K | | P | G | G | G | G | A | N | L | K | G | D | R | S | R | L | L | R |
| bovine proCNP | G | D | K | | P | G | G | G | G | A | N | L | K | D | D | R | S | R | L | L | R |
| sheep proCNP | G | D | K | | P | G | G | G | G | A | N | L | K | D | D | R | S | R | L | L | R |
| mouse proCNP | G | D | K | | P | G | G | G | G | A | N | L | K | G | D | R | S | R | L | L | R |
| pig proCNP | G | D | K | | P | G | G | G | G | A | N | L | K | G | D | R | S | R | L | L | R |

As can be seen, there are several deviations (marked red) from the human sequences. Although even a small number of differences of the amino acid sequence may result in a failure of the human assay, it surprisingly turned out that this was not the case for the present invention.

For example an NT-proANP antibody targeted at AA 1-30 of human NT-proANP, does not recognise the respective canine sequence, although there are significant homologies to the canine sequence Surprisingly human NT-proCNP ELISA antibodies showed excellent performance when tested on septic samples of canine or feline origin. The experiments and results are described in more detail below.

Materials & Methods

Basically the tests were performed as stated in the package insert of the human NT-proCNP ELISA kit (BI-20872) without further modification. Briefly the method includes the following steps:

1. Sample Collection:

Samples were taken from non fasting subjects into VACU-ETTE® (Greiner Bio-One) tubes by veni-puncture: EDTA tubes: 9 ml. The tubes were kept at 4° C. until plasma separation (Centrifugation parameters: 20 min at 2000×g, at 4° C.). All samples were immediately put at −20° C. after separation and assayed together in one assay run.

2. ELISA Procedure:

Add 50 µl STD/SAMPLE/CTRL (Standard/Sample/Control) in duplicate into respective wells, except blank.

Add 200 µl CONJ (anti NT-proCNP—HRPO) into each well, except blank; swirl gently.

Cover tightly and incubate at room temperature (18-26° C.) for 4 hours in the dark.

Aspirate and wash wells 5× with 300 µl diluted WASHBUF (Wash buffer); remove remaining WASHBUF by hitting plate against paper towel after the final washing step.

Add 200 µl SUB (Substrate, Tetramethylbenzidine) into each well. Incubate for 30 min at room temperature (18-26° C.) in the dark. Add 50 µl STOP (Stop solution, 1N $H_2SO_4$) into each well.

Measure absorbance immediately at 450 nm with reference 620 nm, if available.

Results & Discussion

By assaying 13 normal and septic animals each with the method described above, the results depicted in the table below were generated. From the experience with NT-proBNP measurements it was expected, that dogs and cats show similar immune-reactivity. There the analysis was not matched to species.

TABLE 5

Results from animal trials

|  | Species | NT-proCNP pmol/L | Age | Sex |  | Species | NT-proCNP pmol/L | Age | Sex |
|---|---|---|---|---|---|---|---|---|---|
| nor01 | Dog | 0.0 | 1.0 | m | Seps01 | Dog | 1.1 | 12 | m |
| nor02 | Dog | 0.0 | 12.0 | f | Seps02 | Dog | 6.4 | 14 | m |
| nor03 | Dog | 0.2 | 4.0 | m | Seps03 | Dog | 1.1 | 7 | f |
| nor04 | Dog | 0.0 | 4.0 | f | Seps04 | Dog | 5.0 | 11 | f |
| nor05 | Dog | 0.0 | 6.0 | f | Seps05 | Dog | 0.3 | 1 | m |
| nor06 | Dog | 0.0 | 15.0 | m | Seps06 | Dog | 16.8 | 10 | m |
| nor07 | Dog | 0.0 | 1.0 | f | Seps07 | Dog | 0.0 | 1 | f |
| nor08 | Dog | 0.0 | 7.0 | f | Seps08 | Dog | 0.0 | 6 | f |
| nor09 | Dog | 0.0 | 4.0 | f | Seps09 | Dog | 5.2 | 11 | m |
| nor10 | Dog | 0.0 | 5.0 | m | Seps10 | Dog | 26.5 | 8 | f |
| nor11 | Dog | 4.0 | 0.6 | f | Seps11 | Dog | 22.6 | 0.18 | f |
| nor12 | Dog | 0.0 | 2.0 | f | Seps12 | Dog | 9.9 | 11 | f |
| nor13 | Dog | 0.9 | 0.5 | m | Seps13 | cat | 8.6 | 12 | f |

TABLE 6

Summary and analysis of animal results

|  | Assay Results (pmol) | |
|---|---|---|
| Clinical Diagnosis | <0.2 N | >0.3 S |
| N | 11 | 2 |
| S | 0 | 11 |
| Sensitivity | 82% | |
| Specificity | 100% | |

Abbreviations:
N Normal,
S Septic
Norxx Normal sample,
Sepsxx septic sample

As can be seen from the data above the ELISA is capable of detecting sepsis in those animals with excellent specificity and sensitivity.

The two normal samples showing levels above cut off (0.2 µmol/L) may be the result of the low age of the animals (0.5 and 0.6 years), which has been shown for NT-proCNP also in the humans system.

With these experiments, it is evident that CNP is an excellent marker for sepsis and that CNP, especially NT-proCNP, measurements are a valuable new tool for sepsis detection and therapy control in humans and animals.

The invention claimed is:

1. A method for diagnosing septic complications in a polytraumatised human or animal patient, said patient being free of traumatic brain injury, by determining the level of the C-type natriuretic peptide (CNP), or its precursors or the N-terminal fragment of the precursor of the C-type natriuretic peptide (NTproCNP), in a sample of this patient and diagnosing the patient as having septic complications or being at risk of developing septic complications, if the level of CNP, its precursors or the N-terminal fragment, is increased compared to normal levels.

2. Method according to claim 1, characterized in that the patient is an animal patient selected from the group consisting of a cattle, deer, zoo animal, pet, laboratory animal, working animal, bovine, sheep, goat, horse, donkey, yak, pig, rat, mouse, cat, dog, hamster, fish, frog, guinea pig, elephant, bear and monkey patient.

3. Method according to claim 1, characterized in that the patient is a human patient.

4. Method according to claim 1 characterised in that the sample is a blood, serum or plasma sample of the patient.

5. Method according to claim 1, characterized in that the normal level is the level of a patient without having septic complications or without being at risk of developing septic complications.

6. Method according to claim 1, characterized in that the patient is diagnosed to have septic complications or is at risk of developing septic complications, if the level of NT-proCNP is higher than 4 pm (picomol/l).

7. Method according to claim 1, characterized in that CNP is determined by using anti-NT-proCNP antibodies.

8. Method according to claim 1, characterized in that CNP is determined by using an immunoassay kit for human or animal NT-proCNP.

* * * * *